United States Patent [19]

Rossmann et al.

[11] Patent Number: 5,020,542

[45] Date of Patent: Jun. 4, 1991

[54] METHOD OF MEASURING SKIN SENSITIVITY TO ELECTRICAL STIMULATION

[76] Inventors: Charles Rossmann; Tatiana Rossmann, both of Medical Arts Plaza, 214 17th St., Huntingburg, Ind. 47542

[21] Appl. No.: 509,713

[22] Filed: Apr. 16, 1990

[51] Int. Cl.$^5$ ............................................. A61B 15/05
[52] U.S. Cl. ..................................... 128/741; 128/421
[58] Field of Search ............... 128/741, 742, 743, 421, 128/422

[56] References Cited

U.S. PATENT DOCUMENTS

| | | | |
|---|---|---|---|
| 3,364,929 | 1/1968 | Ide et al. | 128/741 |
| 4,305,402 | 12/1981 | Katims | 128/741 |
| 4,387,723 | 6/1983 | Atlee, III et al. | 128/741 |
| 4,595,018 | 6/1986 | Rantala | 128/741 |
| 4,807,643 | 2/1989 | Rosier | 128/741 |
| 4,815,475 | 3/1989 | Burger | 128/741 |

*Primary Examiner*—Francis Jaworski
*Assistant Examiner*—George Manuel
*Attorney, Agent, or Firm*—Leon Gilden

[57] ABSTRACT

A method is set forth to detect, monitor, predetermine, and record a patient's skin sensitivity to electrical stimulation to determine an individual patient's threshold sensitivity to such stimulation. A first application of the invention utilizes a plurality of operators, wherein a first operator manually increases electrical current to an associated patient directed to the patient through an electrode, while the second operator records and charts the response of the aforenoted patient. A further version of the invention utilizes a single operator, wherein a tape recorder to effect recording or response of a patient relative to a stimulating electrical current directed to the patient through an amplified circuit is utilized. A further version of the invention utilizes an automatic step generator to direct current to the patient, wherein the patient utilizes an on/off switch to effect cessations of current subsequent to a threshold of skin sensitivity being attained.

3 Claims, 5 Drawing Sheets

PRIOR ART

METHOD OF MEASURING SKIN SENSITIVITY TO ELECTRICAL STIMULATION

BACKGROUND OF THE INVENTION

2. Field of the Invention

The field of invention relates to skin sensitivity measurements, and more particularly pertains to a new and improved method of measuring skin sensitivity to electrical stimulation wherein the same accurately and precisely records a patient's sensitivity to electrical stimulation.

2. Description of the Prior Art

Predetermined knowledge of skin sensitivity is utilized in a variety of medical applications prior to application of a variety of medial treatments utilizing electrical energy. Heretofore, however, skin sensitivity has been considered a constant value and accordingly misapplication of quantitative and qualitative electrical energy directed to a patient results in a misapplication and misuse of such medical tools. Prior art skin sensitivity tests have typically utilized mechanical prick stimulation or electrical stimulators with controlled voltage or current. It has been determined, however, that skin sensitivity is at variance relative to various portions of an individual's body, and furthermore that skin sensitivity is subject to change in minimal time sequences. Accordingly, skin sensitivity immediately prior to medical application of electrical energy to a patient is required to ascertain an individual's skin sensitivity to a particularized location and a particularized time interval prior to medical treatment. Examples of prior art medical treatments utilizing electrical stimulation may be found in U.S. Pat. No. 4,690,142 to Ross, et al. wherein a method for biofeedback training of an individual to produce tactile sensations on the skin is provided where one or more electrical characteristics and sensations thereof is experienced by the individual to alter a condition to modify the tactile sensation resultant from the electrical stimulation.

U.S. Pat. No. 4,811,742 to Hassel, et al. sets forth electrical stimulation of a muscle group on an individual when provided for re-education and/or appplification of muscle control where motor control has suffered impairment due to injury and the like.

U.S. Pat. No. 4,667,513 to Konno sets forth a method and apparatus for detecting muscle fatigue based on an input signal directed from a patient to a recorder apparatus.

U.S. Pat. No. 3,656,474 to Gentry, et al. sets forth an electrical diagnosis method and apparatus wherein electrical impulse is received from transducers applied to a skin surface of an individual and recorded within a recording apparatus of the organization.

U.S. Pat. No. 4,763,666 to Strian, et al. sets forth the use of electrical current and recording to measure thermal sensitivity of the human peripheral nervous system directed throughout the skin surface of an individual to effect recording of sensation felt by heat or cold application to an individual.

As such, it may be appreciated that there continues to be a need for a new and improved method of measuring skin sensitivity to electrical stimulation wherein the same addresses both the problems of ease of use as well as effectiveness in coordination and construction to properly determine relative skin sensitivity on an individual at a predetermined time interval and in this respect, the present invention substantially fulfills this need.

SUMMARY OF THE INVENTION

In view of the foregoing disadvantages inherent in the known types of methods of measuring skin sensitivity now present in the prior art, the present invention provides a method of measuring skin sensitivity to electrical stimulation wherein the same directs stepped electrical stimulation to a skin surface of an individual to ascertain at a predetermined time interval skin sensitivity of an individual. As such, the general purpose of the present invention, which will be described subsequently in greater detail, is to provide a new and improved method of measuring skin sensitivity to electrical stimulation which has all the advantages of the prior art methods of measuring skin sensitivity and none of the disadvantages.

To attain this, the present invention provides a method setting forth detection, monitoring, predetermination and recordation of a patient's skin sensitivity to electrical stimulation to determine an individual patient's threshold sensitivity to such stimulation. A first application of the invention utilizes a plurality of operators, wherein a first operator manually increases electrical current to an associated patient directed to the patient through an electrode, while the second operator records and charts the response of the aforenoted patient. A further version of the invention utilizes a single operator, wherein a tape recorder to effect recording or response of a patient relative to a stimulating electrical current directed to the patient through an amplified circuit is utilized. A further version of the invention utilizes an automatic step generator to direct current to the patient, wherein the patient utilizes an on/off switch to effect cessations of current subsequent to a threshold of skin sensitivity being attained.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved method of measuring skin sensitivity to electrical stimulation which has all the advantages of the prior art methods of measuring skin sensitivity and none of the disadvantages.

It is another object of the present invention to provide a new and improved method of measuring skin sensitivity to electrical stimulation which may be easily and efficiently manufactured and marketed.

It is a further object of the present invention to provide a new and improved method of measuring skin sensitivity to electrical stimulation which is of a durable and reliable construction.

An even further object of the present invention is to provide a new and improved method of measuring skin sensitivity to electrical stimulation which is susceptible of a low cost of manufacture with regard to both materials and labor, and which accordingly is then susceptible of low prices of sale to the consuming public, therreby making such methods of measuring skin sensitivity to electrical stimulation economically available to the buying public.

Still yet another object of the present invention is to provide a new and improved method of measuring skin sensitivity to electrical stimulation which provides in the apparatuses and methods of the prior art some of the advantages thereof, while simultaneously overcoming some of the disadvantages normally associated therewith.

Still another object of the present invention is to provide a new and improved method of measuring skin sensitivity to electrical stimulation wherein the same permits measurement and recording of skin sensitivity of an individual at a predetermined location about the skin surface of that individual at a predetermined time interval to completely and properly measure skin sensitivity of an individual or patient.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
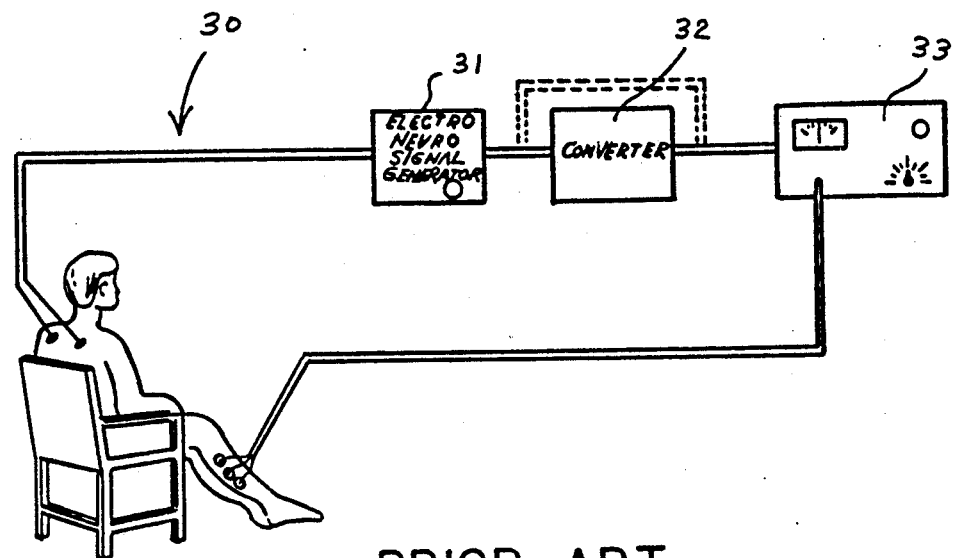
FIG. 1 is an isometric illustration of a prior art bio-feedback system utilizing electrical stimulation.

With reference now to the drawings, and in particular to FIGS. 1 to 6 thereof, a new and improved method of measuring skin sensitivity to electrical stimulation embodying the principles and concepts of the present invention and generally designated by the reference numerals 1-26 will be described.

Figure 2:
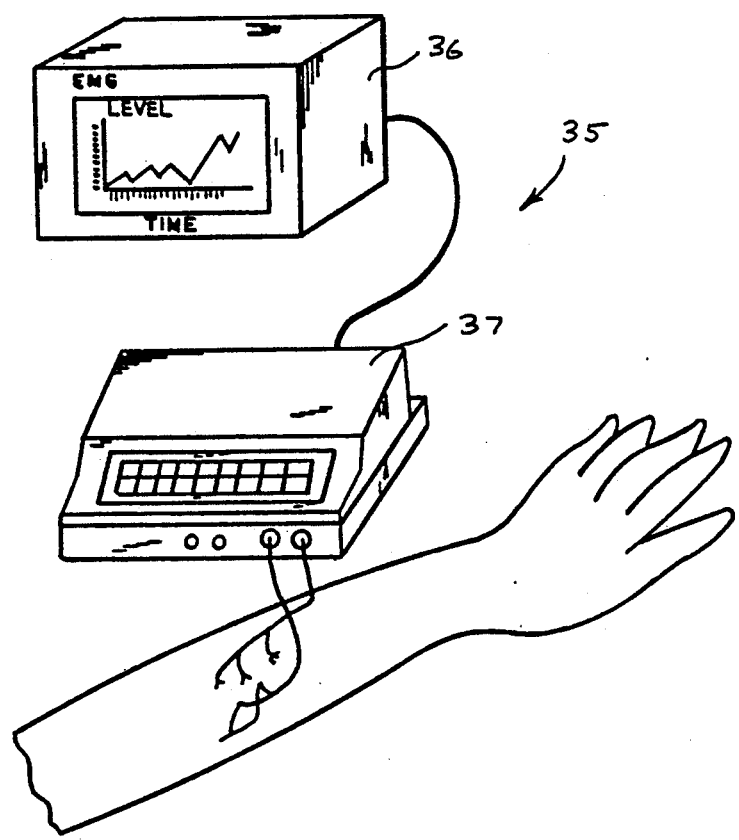
FIG. 2 is an isometric illustration of a further prior art medical treatment utilizing electrical stimulation.

FIG. 1 illustrates a prior art method of utilizing electrical stimulation in a bio-feedback 30 wherein a patient is electrically associated with a signal generator 31 that is controlled by a converter means 40 to provide a proper electrical signal to the generator 31. A control member 33 is operative to control the level of current directed to the individual. FIG. 2 illustrates a further prior art medical treatment organization 35 wherein muscle stimulation to an individual patient is controlled through a console 37 and wherein a monitor 36 is utilized to display a measured electromyogram.

Figure 3:
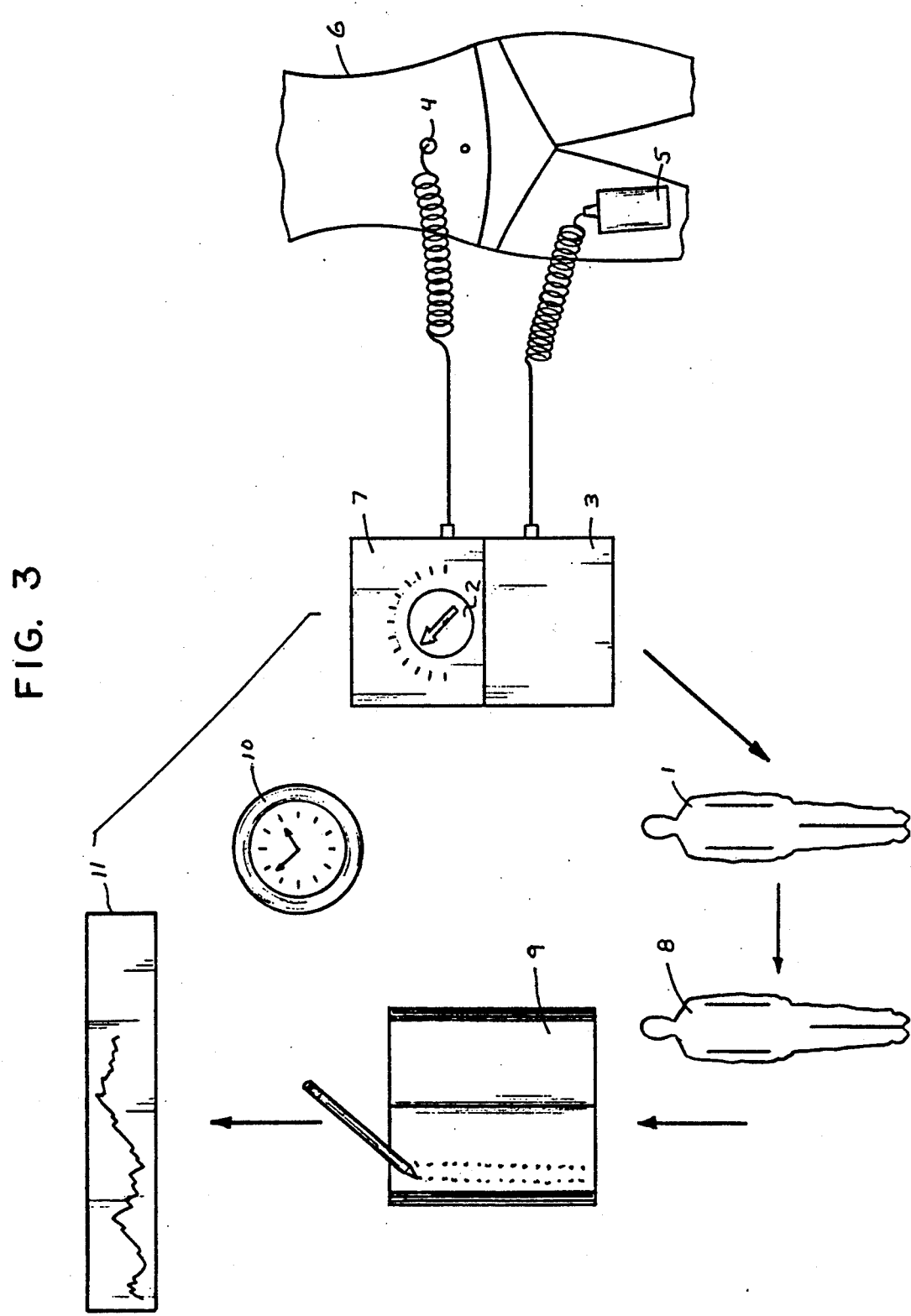
FIG. 3 is a diagrammatic illustration of the method of the instant invention utilizing a plurality of operators.

More specifically, the method of measuring skin sensitivity to electrical stimulation as set forth by the instant invention is illustrated in FIG. 3 utilizing a plurality of operators set forth as a first operator 1 and a second operator 8. The first operator 1 accordingly manually increases a stimulating electrical current directed to a patient 6 by selecting a predetermined level directed through an amplifier, including a current scale 7 associated with a control knob 2. An electrode 4 mounted on the patient skin surface of the patient 6 is grounded through a grounding electrode 5 that completes a circuit from the amplifier or peripheral nerve stimulator 3. Upon the patient 6 expressing irritation by the electrical stimulation, a current value determined from the scale 7 is transmitted to the second operator 8 that in turn inscribes the predetermined value of the scale 7 effecting the irritation into the book or ledger 9. A predetermined time interval determined from a time piece or watch 10 determines the interval in question and various recordings over the predetermined time interval is subsequently transposed onto a graph 11 that is graphed as a function of time versus a current value. A typical stimulating current tuilized is in the form of a single rectangular impulse of a time sequence substantially of two hundred microseconds long and repeating in frequency every second.

Figure 4:
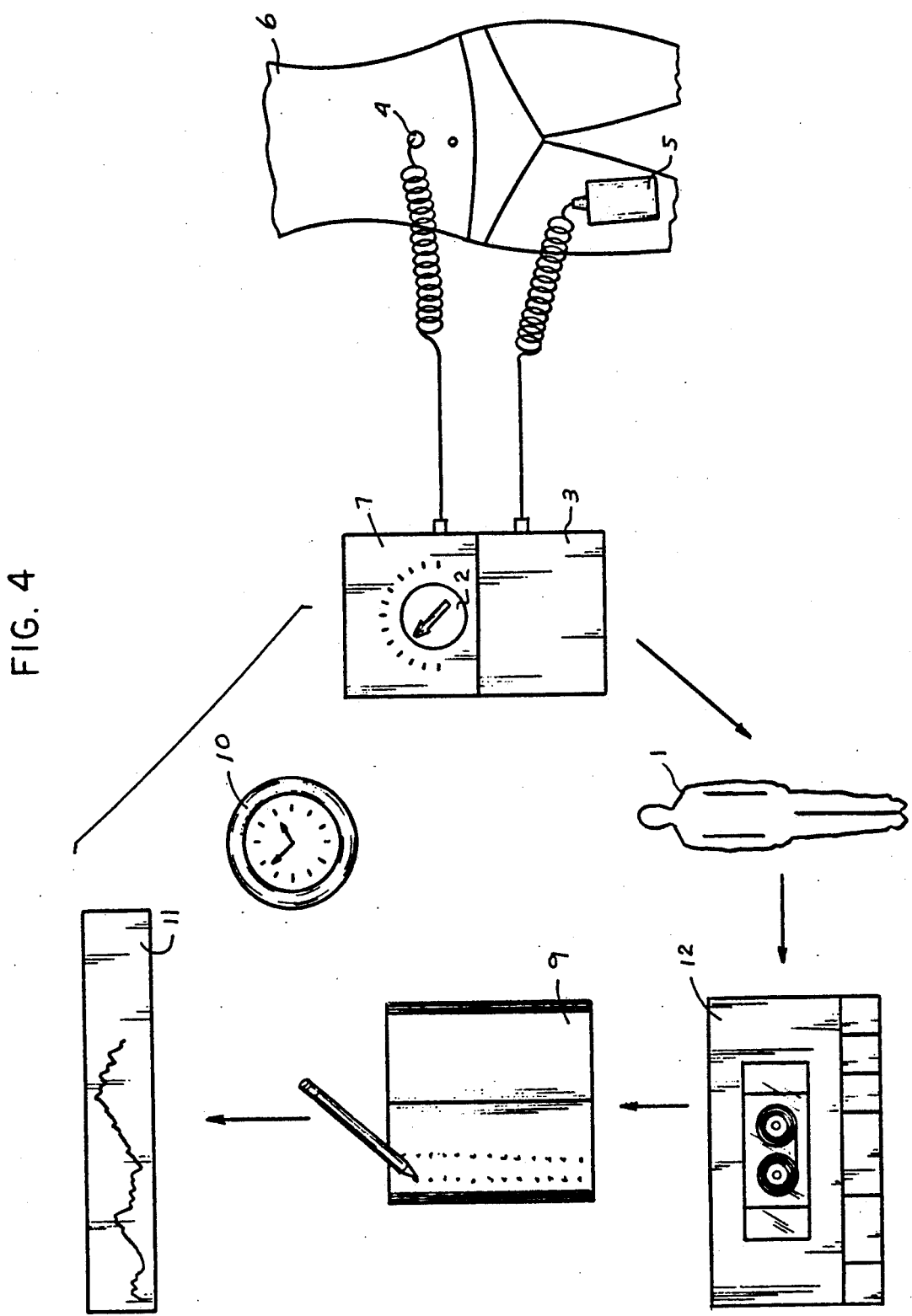
FIG. 4 is a diagrammatic orthographic illustration of the instant invention utilizing a single operator.

FIG. 4 illustrates a single operator effecting utilization of the instant invention. The method as set forth per the use of FIG. 3 is repeated, but in lieu of the second operator 8, a tape recorder 12 is utilized, wherein the first operator 1 dictates the measured values of the threshold stimulating electrical current directed to the patient 6 through the stimulating electrode 4 and the associated grounding electrode 5 utilizing the peripheral nerve stimulator electrical amplifier 3. These measured values are recorded utilizing a predetermined span of time utilizing the watch 10, wherein subsequently the value is dictated into the recorder 12 or transcribed into the ledger or book 9. Subsequently the values directed from the ledger 9 are again mounted in a graph form on the graph 11 in a manner as set forth above.

Figure 5:
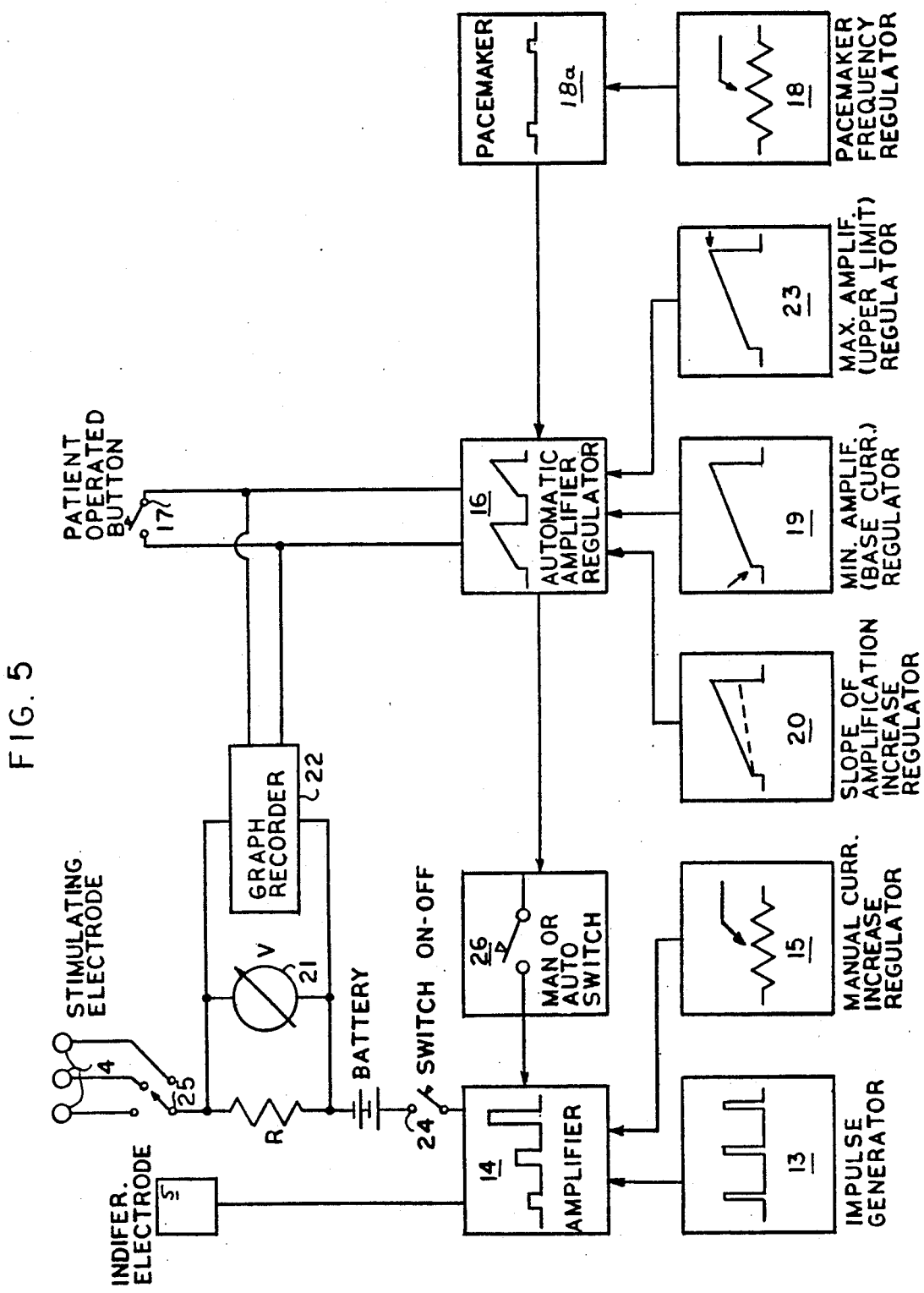
FIG. 5 is a diagrammatic illustration of the instant invention utilizing a patient-only control.
Figure 6:
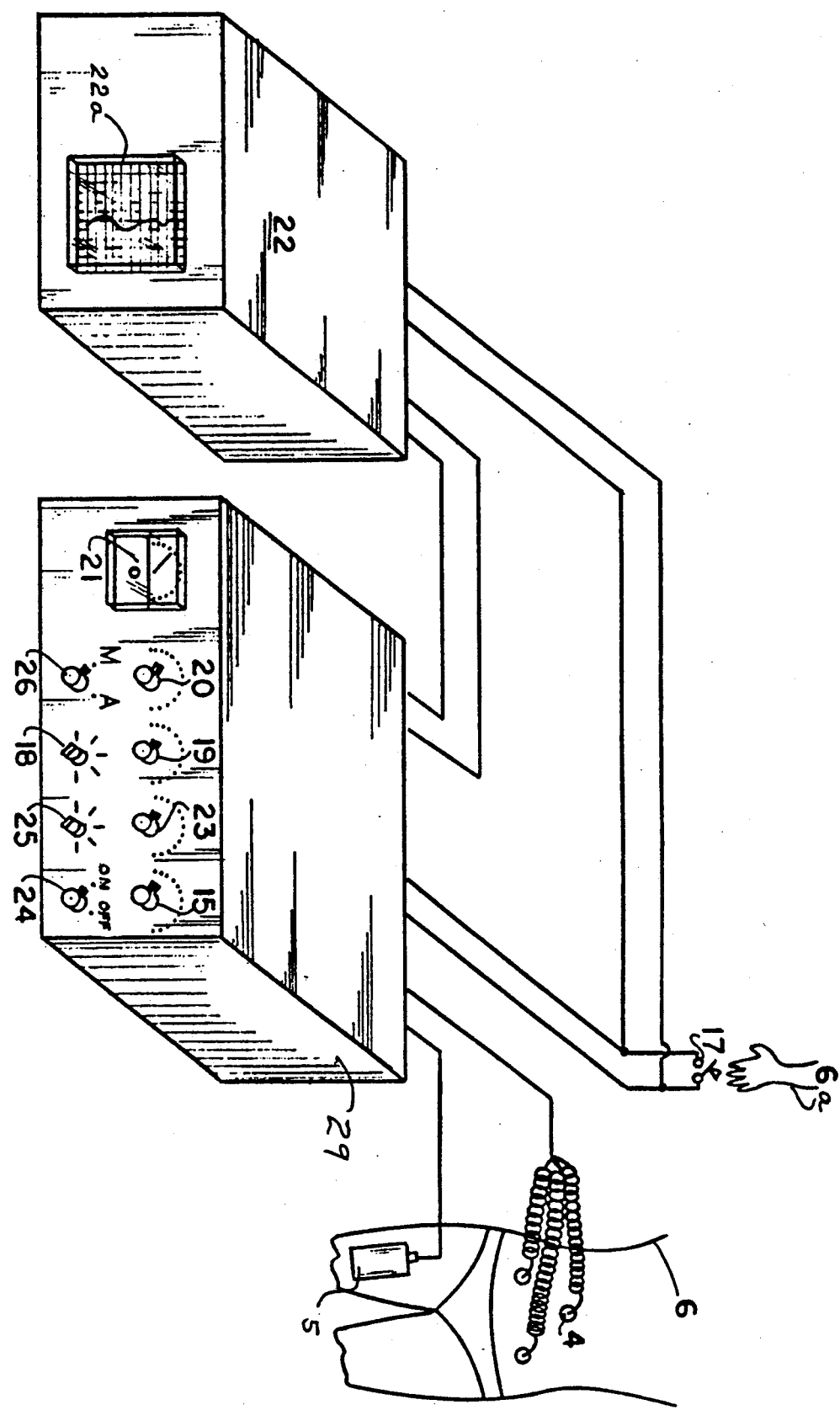
FIG. 6 is an isometric diagrammatic illustration of an automatic version utilizing a single operator.

FIG. 5 illustrates the use of an automatic version of the organization wherein the patient 6 effects cessation of a peripheral nerve stimulating current directed to the patient through the use of a single or plurality of electrodes 4 receiving current from the control unit 29 and directing a peripheral nerve stimulating circuit to the patient 6 utilizing the grounding electrode 5 in a manner as noted above. The electrical amplifier or generator 13 is utilized to produce a series of impulses of current of a rectangular shape that are 0.2 milliseconds long with a frequency of one per second (1 Hz). These currents are directed through the current amplifier 14 amplifying the current through a ratio that may be regulated by the current regulator 15 or by an automatic step amplifier 16 and associated circuit that in regular predetermined intervals increases amplification of the current from zero to a threshold orientation where an associated patient 6 is aware of threshold stimulation of the skin at the positioning of the electrode 4. At that juncture of time, the aforenoted patient 6 engages a switch 17 which ceases further increase of the aforenoted stimulating current and the current will let that juncture immediately return to a zero datum of current directed to the patient. Subsequently after a predetermined time interval, the stimulation of the skin at the electrode 4 orientation will again initiate and again increase in a manner as noted above to again reach the threshold at where the patient 6 engages the switch 7. Alternatively, the minumum amplification control 19 may be utilized to prevent return of the stimulating current to zero but to a lower or preselected datum from which a stimulating current is again amplified or stepped to a position of threshold sensation to the patient. The slope or time related increase of current may also be regulated by the slope control 20. Further, intensity of current impulse directed through the skin electrodes 4 and to the patient 6 is calculated and measured by the peak volt meter 22 and simultaneously recorded on a graphic recorder 22 and the recorder display 22a (see FIG. 6). To ensure that the graph is of a visually understandable and clear depiction of the values of threshold current stimulation values, the recorder 22 continues to record value levels directed from the step amplifier 16 or the manually manipulated regulator 15, the graph continues to record until the switch 17 is depressed and the cycle is again reinitiated. It should also be noted that a stimulating current directed to the patient through the manually controlled amplifier 14 or the automatic stepped amplifier 16 is limited by a limiting regulator 23. Further, the time interval, as noted above, to restart the cycle of directing a stimulating current to the patient may be controlled through a pace maker regulator 18 and controlling pace maker circuit 18a.

Should the organization not be utilized, the stimulating current may be interrupted by the switch 24 to disengage an amplifier circuit directed to the patient. Further, a selector switch 25 may be utilized in conjunction with a plurality of stimulating electrodes 4 to permit selection of different skin locations for electrical stimulation by use of the method of the instant invention. As illustrated in FIG. 5, whether the automatic stepped amplifier and regulator 16 is utilized or the manually amplified apparatus is utilized, it is determined by the amplifier selection switch 26 utilized in a conventional manner to select between a plurality of amplification sources.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of measuring skin sensitivity to electrical stimulation comprising, providing and positioning a plurality of electrical directing electrode members at spaced orientations onto a preselected skin surface of an individual, and providing an electrical directing grounding electrode on the individual spaced from the plurality of electrical directing electrode members, and providing a nerve stimulating electrical amplifier member to direct a nerve stimulating electrical current at a predetermined amplitude to the individual through the electrode member and the grounding electrode to effect skin stimulation of the skin surface whereby the individual is made aware of the skin stimulation, and directing a cycle of a predetermined impulse and amplitude of nerve stimulating electrical current to the individual over a predetermined time, and repeating the cycle to provide a plurality of cycles, and providing a recording means for plotting the cycles as a function of time, versus a current amplitude, and plotting the cycles as a function of time versus current amplitude, and wherein the step of providing a nerve stimulating electrical amplifier includes providing the amplifier with an adjustment control to adjust the current amplitude, and whrein the amplifier member includes a manually manipulatable current amplifier and further providing an automatic step amplifier to automatically increase the current amplitude at predetermined incremental increases and amplitude, and providing the individual with a first switch, wherein the individual selectively engages the switch to cease directing of the nerve stimulating electrical current to the individual upon the individual made aware of the skin stimulation and wherein the individual engaging the first switch simultaneously resets the amplifier member to permit repeating of the cycle.

2. A method as set forth in claim 1 further including the step of directing the nerve stimulating electrical current to the individual is in a pulse of a rectangular shape and 0.2 milliseconds long with a frequency one pulse per second.

3. A method as set forth in claim 2 including the step of providing the amplifier member with a limit regulator to limit the amplitude of the nerve stimulating electrical current directed to the individual.

* * * * *